US00PP33403P2

(12) United States Plant Patent
Misato et al.

(10) Patent No.: US PP33,403 P2
(45) Date of Patent: Aug. 24, 2021

(54) ***SENECIO* PLANT NAMED 'SENE SIROHYAKU'**

(50) Latin Name: *Senecio cruentus*
Varietal Denomination: Sene Sirohyaku

(71) Applicants: Tomoya Misato, Shiga (JP); Kiyoshi Miyazaki, Shiga (JP)

(72) Inventors: Tomoya Misato, Shiga (JP); Kiyoshi Miyazaki, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 16/926,753

(22) Filed: Jul. 12, 2020

(51) Int. Cl.
*A01H 5/02* (2018.01)
*A01H 6/14* (2018.01)

(52) U.S. Cl.
USPC ..... Plt./480
CPC ..... *A01H 6/14* (2018.05)

(58) Field of Classification Search
USPC ..... Plt./480
CPC ..... A01H 6/14
See application file for complete search history.

*Primary Examiner* — Anne Marie Grunberg
(74) *Attorney, Agent, or Firm* — C. Anne Whealy

(57) ABSTRACT

A new and distinct cultivar of *Senecio* plant named 'Sene Sirohyaku', characterized by its semi-upright and uniformly mounded plant habit; vigorous growth habit; freely branching habit; freely flowering habit and daisy-type inflorescences with ray florets that are dark purple to red purple in color and disc florets that are dark purple in color.

1 Drawing Sheet

Botanical designation: *Senecio cruentus.*
Cultivar denomination: 'SENE SIROHYAKU'.

BACKGROUND OF THE INVENTION

The present invention relates to a new and distinct cultivar of *Senecio* plant, botanically known as *Senecio cruentus*, and hereinafter referred to by the name 'Sene Sirohyaku'.

The new *Senecio* plant is a product of a planned breeding program conducted by the Inventors in Higashiomi, Shiga, Japan. The objective of the breeding program is to create new semi-upright, uniformly mounding and vigorous *Senecio* plants with a freely-branching habit, early flowering and numerous attractive inflorescences.

The new *Senecio* plant originated from a cross pollination conducted by the Inventors in May, 2012 of a proprietary selection of *Senecio cruentus* identified as code number S10-22E, not patented, as the female, or seed, parent with a proprietary selection of *Senecio cruentus* identified as code number S10-31-2, not patented, as the male, or pollen, parent. The new *Senecio* plant was discovered and selected by the Inventors as a single flowering plant within the progeny of the stated cross-pollination in a controlled greenhouse environment in Higashiomi, Shiga, Japan in February, 2013.

Asexual reproduction of the new *Senecio* plant by terminal cuttings in a controlled greenhouse environment in Higashiomi, Shiga, Japan since October, 2014 has shown that the unique features of this new *Senecio* plant are stable and reproduced true to type in successive generations.

SUMMARY OF THE INVENTION

Plants of the new *Senecio* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sene Sirohyaku'. These characteristics in combination distinguish 'Sene Sirohyaku' as a new and distinct *Senecio* plant:

1. Semi-upright and uniformly mounded plant habit.
2. Vigorous growth habit.
3. Freely branching habit.
4. Freely flowering habit.
5. Daisy-type inflorescences with ray florets that are dark purple to red purple in color and disc florets that are dark purple in color.

Plants of the new *Senecio* can be compared to plants of the female parent selection. Plants of the new *Senecio* differ primarily from plants of the female parent selection in ray floret color as plants of the new *Senecio* have dark purple to red purple-colored ray florets whereas plants of the female parent selection have red-colored ray florets.

Plants of the new *Senecio* can be compared to plants of the male parent selection. Plants of the new *Senecio* differ primarily from plants of the male parent selection in ray floret color as plants of the new *Senecio* have dark purple to red purple-colored ray florets whereas plants of the male parent selection have bluish-colored ray florets.

Plants of the new *Senecio* can also be compared to plants of *Senecio cruentus* 'Sunsenegoroku', disclosed in U.S. Plant Pat. No. 27,975. In side-by-side comparisons, plants of the new *Senecio* differ from plants of 'Sunsenegoroku' in the following characteristics:

1. Plants of the new *Senecio* are not as upright as plants of 'Sunsenegoroku'.
2. Plants of the new *Senecio* have smaller leaves than plants of 'Sunsenegoroku'.

3. Plants of the new *Senecio* are more freely flowering than plants of 'Sunsenegoroku'.
4. Plants of the new *Senecio* have larger inflorescences than plants of 'Sunsenegoroku'.
5. Inflorescences of plants of the new *Senecio* are flatter than inflorescences than plants of 'Sunsenegoroku'.
6. Plants of the new *Senecio* and 'Sunsenegoroku' differ in ray floret color as plants of the new *Senecio* have dark purple to red purple-colored ray florets whereas plants of 'Sunsenegoroku' have violet blue-colored ray florets.

BRIEF DESCRIPTION OF THE PHOTOGRAPHS

The accompanying photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant.

The photograph at the top of the sheet is a side perspective view of a typical flowering plant of 'Sene Sirohyaku' grown in a container.

The photograph at the bottom of the sheet is a close-up view of a typical flowering plant of 'Sene Sirohyaku'.

DETAILED BOTANICAL DESCRIPTION

The aforementioned photographs, following observations and measurements describe plants grown during the winter and spring in 24-cm containers in an outdoor nursery in Higashiomi, Shiga, Japan and under cultural practices typical of commercial *Senecio* production. During the production of the plants, day temperatures averaged 10° C. and night temperatures averaged 5° C. Measurements and numerical values represent averages for typical flowering plants. Plants were six months old when the photographs and the detailed description were taken. In the following description, color references are made to The Royal Horticultural Society Colour Chart, 2015 Edition, except where general terms of ordinary dictionary significance are used.

Botanical classification: *Senecio cruentus* 'Sene Sirohyaku'.

Parentage:

*Female, or seed, parent*.—Proprietary selection of *Senecio cruentus* identified as code number S10-22E, not patented.

*Male, or pollen, parent*.—Proprietary selection of *Senecio cruentus* identified as code number S10-31-2, not patented.

Propagation:

*Type*.—Terminal vegetative cuttings.

*Time to initiate roots, summer and winter*.—About one week at temperatures about 18° C. to 20° C.

*Time to produce a rooted young plant, summer and winter*.—About four weeks at temperatures about 18° C. to 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching.

Plant description:

*Plant form and growth habit*.—Semi-upright and uniformly mounded plant habit; daisy-type inflorescences positioned above the foliar plane; freely branching habit; vigorous growth habit; freely branching habit with about seven primary lateral branches with numerous secondary branches.

*Plant height*.—About 22.5 cm.

*Plant diameter*.—About 43 cm.

*Lateral branches*.—Length: About 16.5 cm. Diameter: About 5.8 mm. Internode length: About 1.9 cm. Strength: Strong. Aspect: Mostly upright. Texture: Sparsely pubescent. Color: Close to 144C tinged with close to between 197A and 199A.

*Leaf description*.—Arrangement: Alternate, simple. Length: About 5.3 cm. Width: About 6.4 cm. Shape: Cordate. Apex: Acute. Base: Cordate. Margin: Crenate to serrate, slightly undulate. Texture, upper surface: Sparsely pubescent. Texture, lower surface: Densely pubescent. Venation pattern: Pinnate; reticulate. Color: Developing leaves, upper surface: Close to 137B. Developing leaves, lower surface: Close to 147B. Fully expanded leaves, upper surface: Close to 137A; venation, close to 145B. Fully expanded leaves, lower surface: Close to 147B; venation, close to 145B tinged with close to N77D. Leaf petioles: Length: About 5.5 cm. Diameter: About 2 mm. Texture, upper and lower surfaces: Pubescent. Color, upper surface: Close to 145C tinged with close to N77C. Color, lower surface: Close to 145B tinged with close to N77C.

Inflorescence description:

*Appearance*.—Daisy-type inflorescences with lanceolate-shaped ray florets; inflorescences arising from upper leaf axils and positioned above the foliar plane on strong peduncles; disc and ray florets developing acropetally on a capitulum; inflorescences face mostly upright to outwardly; freely flowering habit with about 90 inflorescences developing per plant.

*Fragrance*.—None detected.

*Natural flowering season*.—Plants of the new *Senecio* begin flowering about 22 weeks after planting; plants flower continuously from winter to late spring in Japan.

*Inflorescence longevity*.—Inflorescences last about two weeks on the plant; inflorescences persistent.

*Inflorescence buds*.—Height: About 1.9 cm. Diameter: About 7.2 mm. Shape: Globose. Color: Close to 83A; proximally, close to N78A.

*Inflorescence size*.—Diameter: About 5.7 cm. Depth (height): About 1 cm. Disc diameter: About 1.3 cm.

*Receptacles*.—Diameter: About 7.3 mm. Height: About 1.7 mm. Color: Close to 145C.

*Ray florets*.—Quantity and arrangement: About 13 per inflorescence arranged in a single whorl. Length: About 2.4 cm. Width: About 6 mm. Shape: Lanceolate. Apex: Obtuse. Base: Obtuse. Margin: Entire, not undulate. Aspect: Initially upright, then horizontal; flat. Texture, upper and lower surfaces: Shallowly ridged, glabrous. Color: When opening, upper surface: Close to 83A; proximally, close to NN78A. When opening, lower surface: Close to N82A, 83B and N82D. Fully opened, upper surface: Initially, close to 83A becoming closer to 72A and NN78A; color does not change with development. Fully opened, lower surface: Close to N82A, 83B and N82D.

*Disc florets*.—Quantity per inflorescence: About 99. Length: About 9.1 mm. Diameter, at apex: About 2.1 mm. Diameter, at base: About 1 mm. Shape: Tubular; apex dentate, five-pointed. Texture: Smooth, glabrous. Color, immature and mature: Close to 79A.

*Phyllaries*.—Quantity and arrangement: About 13 per inflorescence arranged in a single whorl. Length: About 5.6 mm. Width: About 2.2 mm. Shape: Lanceolate. Apex: Narrowly acute. Base: Fused. Margin: Entire. Texture, upper and lower surfaces: Smooth, glabrous. Color, upper surface: Close to 143A. Color, lower surface: Close to 138A.

*Peduncles*.—Length: About 6.3 cm. Diameter: About 1.5 mm. Strength: Strong. Aspect: Mostly upright. Texture: Smooth, glabrous. Color: Distally, close to 144A; proximally, close to 144B tinged with close to N187B.

*Reproductive organs*.—Androecium: Present on disc florets only. Filament length: About 1.1 mm. Filament color: Close to NN155B. Anther size: About 2.1 mm by 0.4 mm. Anther shape: Narrowly ellipsoidal. Anther color: Close to N79B; at the apex, close to N79A. Pollen amount: Moderate. Pollen color: Close to 13A. Gynoecium: Present on both ray and disc florets. Pistil length: About 9.2 mm. Stigma shape: Bi-parted. Stigma color: Close to N79A. Style color: Distally, closer to 77A; proximally, close to 157D. Ovary color: Close to 157D.

*Seeds and fruits*.—To date, seed and fruit development have not been observed on plants of the new *Senecio*.

disease & pest resistance: To date, plants of the new *Senecio* have not been observed to be resistant to pathogens and pests common to *Senecio* plants.

Temperature tolerance: Plants of the new *Senecio* have been observed to tolerate temperatures ranging from about 0° C. to about 30° C.

It is claimed:

1. A new and distinct *Senecio* plant named 'Sene Sirohyaku' as illustrated and described.

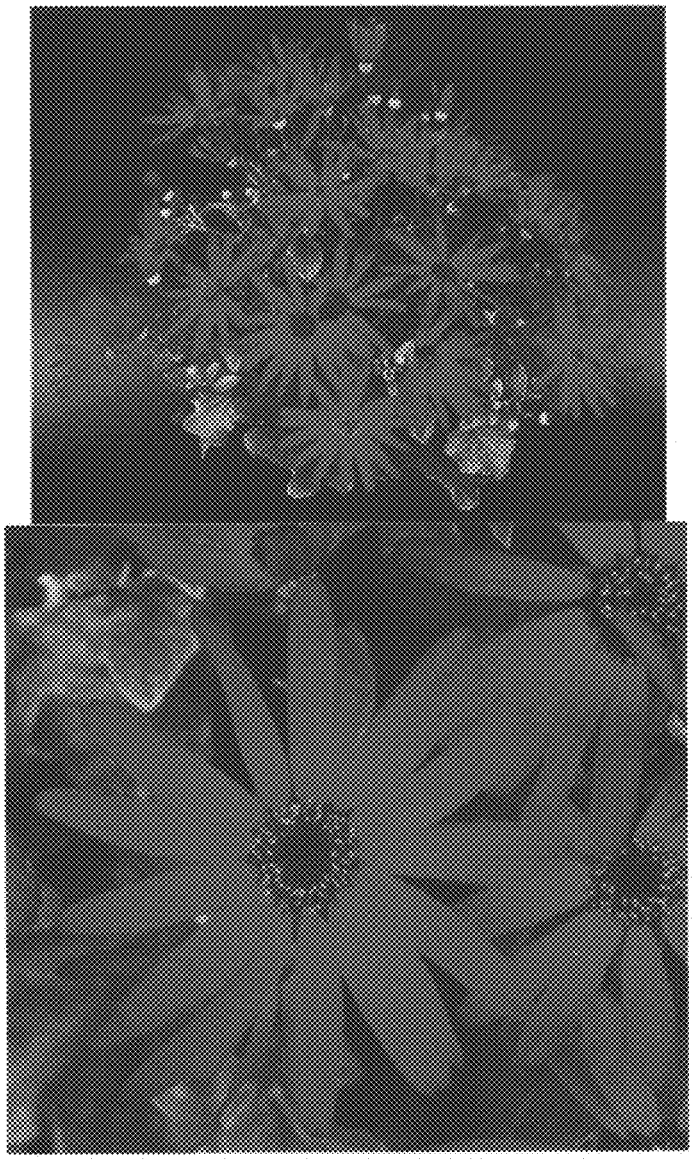

* * * * *